(12) United States Patent
Graham et al.

(10) Patent No.: US 11,358,318 B2
(45) Date of Patent: Jun. 14, 2022

(54) COMPONENT FOR CONVEYING GASES

(71) Applicant: Fisher & Paykel Healthcare Limited, Auckland (NZ)

(72) Inventors: Peter Kenneth Graham, Auckland (NZ); Enrico Alvarez Garcia, Auckland (NZ); Shu-Yi Chu, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 357 days.

(21) Appl. No.: 16/560,743

(22) Filed: Sep. 4, 2019

(65) Prior Publication Data

US 2019/0388640 A1 Dec. 26, 2019

Related U.S. Application Data

(63) Continuation of application No. 13/821,674, filed as application No. PCT/NZ2011/000186 on Sep. 9, 2011, now Pat. No. 10,449,318.

(Continued)

(51) Int. Cl.
*A61M 16/08* (2006.01)
*B29C 48/09* (2019.01)
(Continued)

(52) U.S. Cl.
CPC ............ *B29C 48/09* (2019.02); *A61M 13/006* (2014.02); *A61M 16/0808* (2013.01);
(Continued)

(58) Field of Classification Search
CPC .......... A61M 16/1095; A61M 16/0975; A61M 2207/00; A61M 2205/583; A61M 16/08; A61M 16/1075; A61M 2205/7536; B29C 47/0033; B29C 47/0023; B29C 47/126; B29C 47/20; F16L 53/008
See application file for complete search history.

(56) References Cited

U.S. PATENT DOCUMENTS 2,898,941 A 8/1959 Kilcup
3,299,192 A 1/1967 Lux
(Continued)

FOREIGN PATENT DOCUMENTS

CN 101184522 A 5/2008
DE 10021111 A1 11/2001
(Continued)

OTHER PUBLICATIONS

Japan Patent Office, Japanese Examination Report, received in application No. 2018-0901179, dated Jun. 30, 2020, in 4 pages.
(Continued)

*Primary Examiner* — Margaret M Luarca
(74) *Attorney, Agent, or Firm* — Knobbe, Martens, Olson & Bear, LLP

(57) ABSTRACT

This invention provides for a component forming a part of a breathing tube, or forming the breathing tube, for example as a part of a breathing circuit for respiratory therapy. The component comprising a tubular body having a foamed wall. The foamed wall can be formed from extrusion of a single extrudate. The foamed wall is of a sufficient minimum optical transparency such that, in use, there is enabled the visual detection of a liquid (or condensate that may have formed) within the tubular body.

20 Claims, 8 Drawing Sheets

Related U.S. Application Data

(60) Provisional application No. 61/381,880, filed on Sep. 10, 2010.

(51) Int. Cl.

| | | |
|---|---|---|
| *F16L 11/11* | (2006.01) | |
| *A61M 16/10* | (2006.01) | |
| *A61M 13/00* | (2006.01) | |
| *F16L 53/38* | (2018.01) | |
| *B29C 48/13* | (2019.01) | |
| *B29C 48/30* | (2019.01) | |
| *B29C 48/32* | (2019.01) | |
| *A61M 16/16* | (2006.01) | |
| *B29L 23/00* | (2006.01) | |
| *B29K 105/04* | (2006.01) | |

(52) U.S. Cl.
CPC .... *A61M 16/0875* (2013.01); *A61M 16/1095* (2014.02); *B29C 48/13* (2019.02); *B29C 48/303* (2019.02); *B29C 48/32* (2019.02); *F16L 11/111* (2013.01); *F16L 53/38* (2018.01); *A61M 13/003* (2013.01); *A61M 16/16* (2013.01); *A61M 2205/3633* (2013.01); *A61M 2205/583* (2013.01); *A61M 2205/7545* (2013.01); *A61M 2207/00* (2013.01); *A61M 2207/10* (2013.01); *B29K 2105/04* (2013.01); *B29L 2023/007* (2013.01)

(56) References Cited

U.S. PATENT DOCUMENTS

| | | | |
|---|---|---|---|
| 3,425,976 | A | 2/1969 | Adams et al. |
| 4,000,341 | A | 12/1976 | Matson |
| 4,212,787 | A | 7/1980 | Matsuda et al. |
| 4,419,459 | A | 12/1983 | Melchior |
| 5,020,530 | A | 6/1991 | Miller |
| 5,357,948 | A | 10/1994 | Eilentropp |
| 5,377,670 | A | 1/1995 | Smith |
| 5,611,962 | A | 3/1997 | Garcia et al. |
| 5,640,951 | A | 6/1997 | Huddart et al. |
| 5,932,299 | A | 8/1999 | Katoot |
| 6,044,843 | A | 4/2000 | O'Neil et al. |
| 7,318,713 | B2 | 1/2008 | Xu et al. |
| 10,449,318 | B2 | 10/2019 | Graham et al. |
| 2002/0002976 | A1 | 1/2002 | Smith et al. |
| 2005/0229928 | A1 | 10/2005 | Ivri et al. |
| 2005/0239963 | A1 | 10/2005 | Kitano et al. |
| 2007/0059511 | A1 | 3/2007 | Edwards et al. |
| 2007/0207186 | A1 | 9/2007 | Scanlon et al. |
| 2008/0032079 | A1 | 2/2008 | Sahnoune et al. |
| 2009/0025724 | A1 | 1/2009 | Herron |
| 2009/0165792 | A1 | 7/2009 | Zucchi et al. |
| 2009/0247654 | A1 | 10/2009 | Rajendran et al. |
| 2010/0098928 | A1 | 4/2010 | Britton et al. |
| 2010/0218839 | A1 | 9/2010 | Conley et al. |

FOREIGN PATENT DOCUMENTS

| | | |
|---|---|---|
| EP | 0579384 | 1/1994 |
| EP | 588089 | 3/1994 |
| JP | 6-181990 | 7/1994 |
| JP | 2000-500359 | 1/2000 |
| JP | 2002089756 A | 3/2002 |
| JP | 2008-119239 | 5/2008 |
| JP | 2009-544371 | 12/2009 |
| JP | 2010-138963 | 6/2010 |
| JP | 2013-514849 | 5/2013 |
| WO | WO 03/022342 | 3/2003 |
| WO | WO 2003/022342 A1 | 3/2003 |
| WO | WO 2008/011682 | 1/2008 |
| WO | WO 2011/077250 A1 | 6/2011 |
| WO | WO 2012/033421 | 9/2011 |

OTHER PUBLICATIONS

China National Intellectual Property Administration, Second Office Action, Application No. 201710180096.8, dated Sep. 26, 2019, in 18 pages.
Japanese Patent Office, Notification of Reason for Rejection, Application No. CN 2018-90479, dated Mar. 1, 2021 in 2 pages.
Canadian Examination Search Report, Application No. 2,810,662, dated Sep. 21, 2020, in 4 pages.
Chinese Examination Report; received in Application No. 201710180096.8, dated May 15, 2020, in 14 pages.
Japanese Patent Office, Examination Report, Application No. JP 2018-090479, dated Jan. 22, 2020, in 4 pages.
China National Intellectual Property Administration, Rejection Decision, Application No. 201710180096.8, dated Dec. 10, 2020, in 4 pages.
Canadian Intellectual Property Office, Examination Report, Application No. 2,810,662, dated Feb. 14, 2020, 7 pages.
Canadian Intellectual Property Office, Examination Report, Application No. 2,810,662, dated Jul. 16, 2019, in 3 pages.
European Patent Office, Communication Pursuant to Article 94(3) EPC, Application No. 11 823 834.4-1122, dated Jan. 14, 2021 in 5 pages.
Australian Examination Report No. 1 for AU Application No. 2020244384, dated Jul. 15, 2021.
International Search Report; PCT/NZ2011/000186; dated Jan. 23, 2012; 5 pages.
Written Opinion of the International Searching Authority; PCT/NZ2011/000186, dated Jan. 23, 2012, 6 pages.
Australian Examination Report; dated Aug. 8, 2013; 4 pages.
Examination Report; dated Oct. 22, 2013; 2 pages.
Search Examination Report, dated Oct. 22, 2103; 3 pages.
CN Examination Report; dated Jan. 28, 2015; 6 pages.
Japan Examination Report with English Translation; dated Jun. 24, 2015; 5 pages.
China Second Office Action; 201180049065.X; dated Dec. 14, 2015; 18 pages.
Australia Examination Report; 2015200671; dated Feb. 3, 2016; 4 pages.
Canadian Examination Report received in Application No. 2,810,662, dated Jun. 5, 2017 in 3 pages.
Extended European Search Report received in Application No. 11823834.4 dated Jun. 29, 2017 in 7 pages.
Translation of Notice of Rejection received in Application No. 2016-186271 dated Aug. 28, 2017 in 3 pages.
Examination Report in Australian Application No. 2017200478 dated Dec. 13, 2018 in 4 pages.
Examination Report in Chinese Application No. 201710180096.8 dated Dec. 3, 2018 in 9 pages.
Sakhalkar, "Surface Characterization of LLDPE Film containing Glycerol Monostearate", Jan. 2002, Journal of Plastic Film & Sheeting, vol. 18, pp. 32-43 (Year: 2002).
Michael Tolinski, Additives for Polyolephins, Getting the most out of polypropylene, Chapter 17 pp. 228-229.

COMPONENT FOR CONVEYING GASES

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57.

BACKGROUND OF THE INVENTION

Field of the Invention

The present invention relates to components for medical circuits for conveying gases to and/or from a patient. In one particular aspect, the invention relates to conduits and in particular to breathing tubes for use in an inspiratory and/or expiratory limb of a breathing circuit. In another particular aspect the invention relates to a tube for a surgical insufflation system.

Description of the Related Art

In assisted breathing, particularly in medical applications, gases having high levels of relative humidity are supplied and returned through flexible breathing tubes of a relatively restricted size typically between a range of approximately 10 mm to 25 mm diameter (covering both neonatal and adult applications). Such breathing tubes are ideally very light, resistant to kinking or pinching but also very flexible to ensure the greatest performance and level of comfort for the patient. The light weight of a breathing tube is very important to reduce any forces applied to the patient interface by the weight of the tube. Similarly, breathing tubes must be flexible and able to bend easily to achieve a high level of patient comfort, which in turn can improve patient compliance.

In medical applications, such as with assisted breathing, the gases inhaled by a patient are preferably delivered in a condition having humidity near saturation level and at close to body temperature (usually at a temperature between 33° C. and 37° C.). Condensation or rain-out can form on the inside surfaces of the breathing tubes as the high humidity breathing gases cool and/or come into contact with the relatively cooler breathing tube surface. Breathing gases exhaled by a patient are usually returned fully saturated and flow through an expiratory breathing tube. If the expired gas is allowed to cool as it passes along an expiratory breathing tube, condensation or rain-out may also occur.

Similarly, Continuous Positive Airway Pressure (CPAP) systems or positive pressure ventilation systems that provide patients suffering from obstructive sleep apnoea (OSA) with positive pressure breathing gases, also use breathing tubes for delivering (or removing) inspiratory (and/or expiratory) gases.

Condensate forming in a breathing tube (either inspiratory or expiratory) can be breathed or inhaled by a patient and may lead to coughing fits or other discomfort. Condensation within a breathing tube may also interfere with the performance of connected equipment and ancillary devices and/or various sensors.

Attempts have been made to reduce the adverse effects of condensation by either reducing the level of condensation, or providing collection points for draining condensed liquid from the tubing component. Reducing the condensation or rain-out has generally been achieved by maintaining or elevating the temperature above the dew point temperature of the breathing gas to reduce the formation of condensation. This temperature is typically maintained by a heater wire within the breathing tube, although the rain-out performance of these breathing tubes may not be complete due to a number of factors. Further, previous methods of heating the gases flow to reduce rain-out, typically result in heated tubing that has been expensive and/or difficult to manufacture. Particularly, in 'single use' applications such as typically found in hospital applications, the manufacturing cost of breathing tubes is critically important. It is highly desirable to even further reduce rainout, while preferably maintaining a low production cost, for example, by utilising a manufacturing method that is capable of high production speeds.

Similarly, during laparoscopic surgery with insufflation, it may also be desirable for the insufflation gas (commonly $CO_2$) to be humidified before being passed into the abdominal cavity. This can help prevent 'drying out' of the patient's internal organs, and can decrease the amount of time needed for recovery from surgery. Even when dry insufflation gas is employed, the gas can become saturated as it picks up moisture from the patient's body cavity. The moisture in the gases tends to condense out onto the walls of the medical tubing or discharge limb of the insufflation system. The water vapour can also condense on other components of the insufflation system such as filters. Any vapour condensing on the filter and run-off along the limbs (inlet or exhaust) from moisture is highly undesirable. For example water which has condensed on the walls, can saturate the filter and cause it to become blocked. This potentially causes an increase in back pressure and hinders the ability of the system to clear smoke. Further, liquid water in the limbs can run into other connected equipment which is undesirable.

Therefore, it may be advantageous to provide a component or tube capable of having improved thermal insulative characteristics for reducing likelihood of condensation or rapid build up of liquid within the tubing component.

Further, in attempting to reduce the adverse effects of condensation, it may be useful for any condensation or other build up of liquid within the tubing component to be observable by a patient or their carer; that is, condensation or other liquid within the component or tube can be visually or optically detected. In this manner, providing for visual or optical detection may allow for steps to be taken in managing such liquid condensation or other liquid that may have built up in the tube component. The ability to visually or optically detect such condensation or other liquid build up within the tube component may also have further benefits in terms of managing the passage of gases to or from a patient, or through a tubing component forming a part of a system for passage of gases to or from a patient, or for better managing the treatment for the patient.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Further aspects and advantages of the present invention will become apparent from the ensuing description which is given by way of example only.

SUMMARY OF THE INVENTION

It is an object of the present invention to provide a component and/or method of manufacturing a component that will at least go some way towards improving on the above or which will at least provide the public and the medical profession with a useful choice.

In a first aspect, the present invention may broadly consist in a component forming a part of a breathing tube, or forming the breathing tube, comprising: a tubular body having a foamed wall, wherein the foamed wall is of a sufficient minimum optical transparency such that, in use, enables visual detection of a liquid (or condensate that may have formed) within the tubular body.

Preferably the tubular body having the foamed wall is formed from extrusion of a single extrudate.

In a further aspect, the present invention may broadly consist in a component forming a part of a breathing tube, or forming the breathing tube, comprising: a tubular body having a foamed wall formed from extrusion of a single extrudate, wherein the foamed wall is of a sufficient minimum optical transparency such that, in use, enables visual detection of a liquid (or condensate that may have formed) within the tubular body.

Preferably the wall of the tubular body is corrugated, or of a corrugate profile, wherein the corrugation profile comprises alternating outer crests (or annular protrusions) and inner troughs (or annular recesses). Preferably the outer crests correspond to a location of maximum inner radius and maximum outer radius of the tubular body, and the inner crests correspond to a location of minimum inner radius and minimum outer radius of the tubular body.

Preferably the corrugations may be of an annular corrugation or a spiral corrugation form.

Alternatively preferably the tubular body has a substantially uniform wall thickness.

Preferably the tubular body may have a wall thickness of about 0.2 mm to about 1 mm, or about 0.3 mm to about 0.9 mm, or about 0.4 mm to about 0.8 mm, or about 0.5 mm to about 0.7 mm, or about 0.3 mm to about 0.6 mm, or about 0.4 mm to about 0.7 mm. The wall may be about 0.2, 0.3, 0.4, 0.5, 0.6, 0.7, 0.8, 0.9 or 1 mm thick. Preferably is about 0.4 mm to about 0.8 mm, even more preferably is 0.6 mm thick.

Preferably the foamed wall is thermally insulative of, at least, the interior of the tubular body bounded by the foamed wall. Preferably, the foamed wall has a thermal conductivity of about 0.25 to 0.45 W/m–° K (Watts per meter degrees Kelvin). Even more preferably, the foamed wall has a thermal conductivity of about 0.15 to 0.35 W/m–° K, or about 0.2 to 0.4 W/m–° K. Preferably is about 0.3 W/m–° K.

Preferably the foamed wall is a single-piece of a foamed polymer material.

Preferably the foamed wall has a void fraction of up to about 10%, or up to about 9%, or up to about 8%, or up to about 7%, or up to about 6% or up to about 5%, or up to about 4%, or up to about 3%, or up to about 2%, or up to about 1%. More preferably, the foamed wall has a void fraction of about 1%, of about 1.5%, of about 2%, of about 2.5%, of about 3%, of about 3.5%, of about 4%, or about 4.5%, or about 5%, or about 5.5%, or about 6%, or about 6.5%, or about 7%, or about 7.5%, or about 8%, or about 8.5%, or about 9%, or about 9.5%, or about 10%. Most preferably, is about 5.5% or about 7.5%, or is about 5.5% to about 7.5%.

Preferably the extrudate comprises one or more polymer(s) of Linear Low Density Polyethylene (LLDPE), Low Density Polyethylene (LDPE), Polypropylene (PP), Polyolefin Plastomer (POP), Ethylene Vinyl Acetate (EVA) or blends of these materials. Plasticised PVC may also be a suitable material, but it is not as well accepted for environmental reasons.

Preferably the extrudate comprises one or more chemical foaming agent. More preferably a chemical foaming agent may comprise calcium oxide.

Preferably the extrudate comprises one or more surface modification agent. More preferably a surface modification agent may comprise of one or more of glycerol monostearate (GMS), ethoxylated amine, alkanesulphonate sodium salt, or lauric diethanolamide.

Preferably the polymer comprises at least about 98.4, 98.5, 98.6, 98.7, 98.8, 98.9, 99.0, 99.1, 99.2, 99.3, 99.4, 99.5, 99.6, 99.7, 99.8, or 99.9 weight percent (wt. %) of the total extrudate. Preferably about 98.4 wt. %. More preferably the polymer comprises about 99.49 wt. % of the total extrudate. Alternatively preferably the polymer comprises about 99.488 wt. % of the total extrudate.

Preferably the chemical foaming agent comprises at least about 0.005, 0.006, 0.007, 0.008, 0.009, 0.01, 0.011, 0.012, 0.013, 0.014, 0.015, 0.016, 0.017, 0.018, 0.019, or 0.02 weight percent (wt. %) of the total extrudate. Preferably about 0.005 wt. %. More preferably the chemical foaming agent comprises about 0.01 wt. % of the total extrudate. Alternatively preferably the chemical foaming agent comprises about 0.012 wt. % of the total extrudate. Or, comprises about 0.01 wt. % to about 0.012 wt. %.

Preferably the surface modification agent comprises at least about 0.05, 0.1, 0.15, 0.2, 0.25, 0.3, 0.35, 0.4, 0.45, 0.5, 1.1, 1.2, 1.3, 1.4, or 1.5 weight percent (wt. %) of the total extrudate. Preferably about 0.05 wt. %. More preferably the surface modification agent comprises about 0.25 wt. % of the total extrudate. Alternatively preferably the surface modification agent comprises about 0.5 wt. % of the total extrudate. Alternatively preferably comprises about 0.25 wt. % to about 0.5 wt. % of the total extrudate.

Preferably the wall of the resultant tubular body enables surface property contact angles of less than about 50, 45, 40, 35, 30, 25, 20 degrees (°), as measurable by an angle measurement device such as a geniometer. Preferably is 45°. More preferably, the wall of the resultant tubular body enables surface property contact angles of about 33°.

Preferably the component further comprises a heater. Preferably the heater is associated with a wall of the tubular body. Preferably the heater is associated with an interior wall surface of the tubular body. Preferably the heater is associated with an exterior wall surface of the tubular body. Preferably the heater is embedded, either partially or wholly, in the wall of the tubular body.

Preferably the tubular body further comprises an outer sheath. Preferably the outer sheath surrounds a heater associated with an exterior wall surface of the tubular body. Preferably the outer sheath may trap air between adjacent outer crests (or annular protrusions) and restrains a heater, such as a heater wire, associated with an exterior wall surface of the tubular body.

Preferably the tubular body is a breathing tube and is terminated by a first connector at an inlet and a second connector at an outlet, and wherein only one gases passageway is provided the length between the inlet connector and the outlet connector.

Preferably the tubular body is a component of a conduit for use in at least part of an insufflation system. Preferably the tubular body is a component of a breathing tube for use in a breathing circuit.

Preferably the tubular body is flexible as defined by passing the test for increase in flow resistance with bending according to ISO 5367:2000(E) (Fourth edition, Jun. 1, 2001).

In a further aspect, the present invention may broadly consist in a component forming a part of a breathing tube, or forming the breathing tube, comprising: a tubular body having a foamed wall formed from a single extrudate, and a heater therein, wherein the foamed wall is of a sufficient minimum optical transparency that, in use, enables visual detection of a liquid (or condensate that may have formed) within the tubular body.

Preferably the wall of the tubular body is corrugated, or of a corrugate profile, wherein the corrugation profile comprises alternating outer crests (or annular protrusions) and inner troughs (or annular recesses). Preferably the outer crests correspond to a location of maximum inner radius and maximum outer radius of the tubular body, and the inner crests correspond to a location of minimum inner radius and minimum outer radius of the tubular body.

Preferably the corrugations may be of an annular corrugation or a spiral corrugation form.

Alternatively preferably the tubular body has a substantially uniform wall thickness.

Preferably the tubular body may have a wall thickness of about 0.2 mm to about 1 mm, or about 0.3 mm to about 0.9 mm, or about 0.4 mm to about 0.8 mm, or about 0.5 mm to about 0.7 mm, or about 0.3 mm to about 0.6 mm, or about 0.4 mm to about 0.7 mm. The wall may be about 0.2, 0.3, 0.4, 0.5, 0.6, 0.7, 0.8, 0.9 or 1 mm thick. Preferably is about 0.4 mm to about 0.8 mm, or is 0.6 mm thick.

Preferably the foamed wall is thermally insulative of, at least, the interior of the tubular body bounded by the foamed wall. Preferably, the foamed wall has a thermal conductivity of about 0.25 to 0.45 W/m–° K (Watts per meter degrees Kelvin). Even more preferably, the foamed wall has a thermal conductivity of about 0.15 to 0.35 W/m–° K, or about 0.2 to 0.4 W/m–° K. Preferably is about 0.3 W/m–° K.

Preferably the foamed wall is a single-piece of a foamed polymer material.

Preferably the foamed wall has a void fraction of up to about 10%, or up to about 9%, or up to about 8%, or up to about 7%, or up to about 6% or up to about 5%, or up to about 4%, or up to about 3%, or up to about 2%, or up to about 1%. More preferably, the foamed wall has a void fraction of about 1%, of about 1.5%, of about 2%, of about 2.5%, of about 3%, of about 3.5%, of about 4%, or about 4.5%, or about 5%, or about 5.5%, or about 6%, or about 6.5%, or about 7%, or about 7.5%, or about 8%, or about 8.5%, or about 9%, or about 9.5%, or about 10%. Most preferably, is about 5.5% or about 7.5%, or is about 5.5% to about 7.5%. Preferably is about 5.5% to about 7.5%.

Preferably the tubular body's foamed wall is foamed by physical foaming, or by chemical foaming, or by a combination of both.

Preferably the extrudate comprises one or more polymer(s) of Linear Low Density Polyethylene (LLDPE), Low Density Polyethylene (LDPE), Polypropylene (PP), Polyolefin Plastomer (POP), Ethylene Vinyl Acetate (EVA) or blends of these materials. Plasticised PVC may also be a suitable material, but it is not as well accepted for environmental reasons.

Preferably the extrudate comprises one or more chemical foaming agent. More preferably a chemical foaming agent may comprise calcium oxide.

Preferably the extrudate comprises one or more surface modification agent. More preferably a surface modification agent may comprise of one or more of glycerol monostearate (GMS), ethoxylated amine, alkanesulphonate sodium salt, or lauric diethanolamide.

Preferably the polymer comprises at least about 98.4, 98.5, 98.6, 98.7, 98.8, 98.9, 99.0, 99.1, 99.2, 99.3, 99.4, 99.5, 99.6, 99.7, 99.8, or 99.9 weight percent (wt. %) of the total extrudate. More preferably the polymer comprises about 99.49 wt. % of the total extrudate. Alternatively preferably the polymer comprises about 99.488 wt. % of the total extrudate. Preferably is at least about 98.4 wt. %.

Preferably the chemical foaming agent comprises at least about 0.005, 0.006, 0.007, 0.008, 0.009, 0.01, 0.011, 0.012, 0.013, 0.014, 0.015, 0.016, 0.017, 0.018, 0.019, or 0.02 weight percent (wt. %) of the total extrudate. More preferably the chemical foaming agent comprises about 0.01 wt. % of the total extrudate. Alternatively preferably the chemical foaming agent comprises about 0.012 wt. % of the total extrudate. Or, comprises about 0.01 wt. % to about 0.012 wt. %. Preferably is at least about 0.005 wt. %.

Preferably the surface modification agent comprises at least about 0.05, 0.1, 0.15, 0.2, 0.25, 0.3, 0.35, 0.4, 0.45, 0.5, 1.1, 1.2, 1.3, 1.4, or 1.5 weight percent (wt. %) of the total extrudate. More preferably the surface modification agent comprises about 0.25 wt. % of the total extrudate. Alternatively preferably the surface modification agent comprises about 0.5 wt. % of the total extrudate. Preferably is about 0.25 wt. % to about 0.5 wt. %, or is at least about 0.05 wt. %.

Preferably the wall of the resultant tubular body enables surface property contact angles of less than about 50, 45, 40, 35, 30, 25, 20 degrees (°), by water as measurable by an angle measurement device such as a geniometer. Preferably is 45°. More preferably contact angles of about 20 to about 40 degrees, or about 25 to about 35 degrees, or about 28 to about 33 degrees. Even more preferably, the wall of the resultant tubular body enables surface property contact angles of about 33°.

Preferably the heater is associated with a wall of the tubular body.

Preferably the heater is associated with an interior wall surface of the tubular body. Preferably the heater is associated with an exterior wall surface of the tubular body. Preferably the heater is embedded, either partially or wholly, in the wall of the tubular body.

Preferably the tubular body further comprises an outer sheath. Preferably the outer sheath surrounds a heater associated with an exterior wall surface of the tubular body. Preferably the outer sheath outer trap air between adjacent outer crests (or annular protrusions) and restrains a heater, such as a heater wire, associated with an exterior wall surface of the tubular body.

Preferably the tubular body is a breathing tube and is terminated by a first connector at an inlet and a second connector at an outlet, and wherein only one gases passageway is provided the length between the inlet connector and the outlet connector.

Preferably the tubular body is a component of a conduit for use in at least part of an insufflation system.

Preferably the tubular body is a component of a breathing tube for use in a breathing circuit.

Preferably the tubular body is flexible as defined by passing the test for increase in flow resistance with bending according to ISO 5367:2000(E) (Fourth edition, Jun. 1, 2000).

In a further aspect, the present invention may broadly consist in a component forming a part of a breathing tube, or forming the breathing tube, comprising: a tubular body having a foamed wall formed from a single extrudate, and wherein the foamed wall is surface modified.

Preferably the foamed wall is surface modified by chemical means or physical means.

Preferably the foamed wall is surface modified by altering the surface tension of the wall surface, such as by increasing the surface tension of the wall surface.

Preferably the foamed wall is of a sufficient minimum optical transparency that, in use, enables visual detection of a liquid (or condensate that may have formed) within the tubular body.

Preferably the wall of the tubular body is corrugated, or of a corrugate profile, wherein the corrugation profile comprises alternating outer crests (or annular protrusions) and inner troughs (or annular recesses).

Preferably the tubular body is of an annular corrugation or a spiral corrugation form.

Preferably the outer crests correspond to a location of maximum inner radius and maximum outer radius of the tubular body, and the inner crests correspond to a location of minimum inner radius and minimum outer radius of the tubular body.

Preferably the tubular body has a substantially uniform wall thickness.

Preferably the wall thickness is about 0.2 mm to about 1 mm, or about 0.3 mm to about 0.9 mm, or about 0.4 mm to about 0.8 mm, or about 0.5 mm to about 0.7 mm, or about 0.3 mm to about 0.6 mm, or about 0.4 mm to about 0.7 mm thick.

Preferably the wall thickness is about 0.2, 0.3, 0.4, 0.5, 0.6, 0.7, 0.8, 0.9 or 1 mm thick.

Preferably the foamed wall is thermally insulative of, at least, the interior of the tubular body bounded by the foamed wall.

Preferably the foamed wall has a thermal conductivity of about 0.2 to 0.4 W/m–° K (Watts per meter degrees Kelvin), or about 0.15 to 0.35 W/m–° K, or about 0.25 to 0.45 W/m–° K.

Preferably the foamed wall has a thermal conductivity resistance of about 0.3 W/m–° K.

Preferably the foamed wall is a single-piece of a foamed polymer material.

Preferably the foamed wall has a void fraction of up to about 10%, or up to about 9%, or up to about 8%, or up to about 7%, or up to about 6% or up to about 5%, or up to about 4%, or up to about 3%, or up to about 2%, or up to about 1%.

Preferably the foamed wall has a void fraction of about 1% of about 1.5%, of about 2%, of about 2.5%, of about 3%, of about 3.5%, of about 4%, or about 4.5%, or about 5%, or about 5.5%, or about 6%, or about 6.5%, or about 7%, or about 7.5%, or about 8%, or about 8.5%, or about 9%, or about 9.5%, or about 10%.

Preferably the foamed wall has a void fraction of about 5.5% to about 7.5%.

Preferably the extrudate comprises one or more polymer(s).

Preferably the extrudate comprises one or more of Linear Low Density Polyethylene (LLDPE), Low Density Polyethylene (LDPE), Polypropylene (PP), Polyolefin, Plastomer (POP), Ethylene Vinyl Acetate (EVA), plasticised Polyvinyl chloride (PVC), or blends of these materials.

Preferably the extrudate further comprises one or more chemical foaming agents.

Preferably the extrudate further comprises one or more chemical foaming agents comprising calcium oxide.

Preferably the extrudate further comprises one or more surface modification agents.

Preferably the extrudate further comprises one or more surface modification agents comprising glycerol monostearate (GMS), ethoxylated amine, alkanesulphonate sodium salt, or lauric diethanolamide.

Preferably the extrudate comprises a polymer or polymers being at least about 98.4, 98.5, 98.6, 98.7, 98.8, 98.9, 99.0, 99.1, 99.2, 99.3, 99.4, 99.5, 99.6, 99.7, 99.8, or 99.9 weight percent (wt. %) of the total extrudate.

Preferably the extrudate comprises a polymer or polymers being at least about 99.49 wt. % or 99.4889 wt. % of the total extrudate.

Preferably the extrudate comprises a chemical foaming agent as at least about 0.005, 0.006, 0.007, 0.008, 0.009, 0.01, 0.011, 0.012, 0.013, 0.014, 0.015, 0.016, 0.017, 0.018, 0.019, or 0.02 weight percent (wt. %) of the total extrudate.

Preferably the extrudate comprises a chemical foaming agent as about 0.01 wt. % to 0.012 wt. % of the total extrudate.

Preferably the extrudate comprises a surface modification agent as at least about 0.05, 0.1, 0.15, 0.2, 0.25, 0.3, 0.35, 0.4, 0.45, 0.5, 1.1, 1.2, 1.3, 1.4, or 1.5 weight percent (wt. %) of the total extrudate.

Preferably the extrudate comprises a surface modification agent as about 0.25 wt. % to 0.5 wt. % of the total extrudate.

Preferably the resultant formed tubular body enables surface property contact angles of less than about 50, 45, 40, 35, 30, 25, 20 degrees (°).

Preferably the component further comprises a heater.

Preferably a heater is associated with a wall of the tubular body.

Preferably a heater is associated with an interior wall surface of the tubular body.

Preferably a heater is associated with an exterior wall surface of the tubular body.

Preferably a heater is embedded, either partially or wholly, in the wall of the tubular body.

Preferably the tubular body further comprises an outer sheath.

Preferably the outer sheath surrounds a heater associated with an exterior wall surface of the tubular body.

Preferably the outer sheath outer traps air between adjacent outer crests (or annular protrusions) and restrains a heater, such as a heater wire, associated with an exterior wall surface of the tubular body.

Preferably the tubular body is a breathing tube and is terminated by a first connector at an inlet and a second connector at an outlet, and wherein only one gases passageway is provided the length between the inlet connector and the outlet connector.

Preferably the tubular body is a component of a conduit for use in at least part of an insufflation system.

Preferably the tubular body is a component of a breathing tube for use in a breathing circuit.

Preferably the tubular body is flexible as defined by passing the test for increase in flow resistance with bending according to ISO 5367:2000(E) (Fourth edition, Jun. 1, 2000).

In a further aspect, the present invention may broadly consist in a component forming a part of a breathing tube, or forming the breathing tube, comprising:

a tubular body having a foamed wall, the tubular body formed from a single extrudate. In respect of this aspect, the preferred embodiments as previously described above may be additionally combined with such a tubular body.

In a further aspect, the present invention may broadly consist in a component forming a part of a breathing tube, or forming the breathing tube, comprising: a tubular body having a foamed wall, the tubular body formed from a single extrudate, the tubular body further comprising of an outer sheath. In respect of this aspect, the preferred embodiments as previously described above may be additionally combined with such a tubular body.

In a further aspect, the present invention may broadly consist in a component forming a part of a breathing tube, or forming the breathing tube, comprising: a tubular body having a wall with a modified surface, the tubular body formed from a single extrudate. In respect of this aspect, the preferred embodiments as previously described above may be additionally combined with such a tubular body.

In a further aspect, the present invention may broadly consist in a component forming a part of a breathing tube, or forming the breathing tube, comprising: a tubular body having a wall with a modified surface, the tubular body formed from a single extrudate, the tubular body further comprising of an outer sheath. In respect of this aspect, the preferred embodiments as previously described above may be additionally combined with such a tubular body.

In a further aspect, the present invention may broadly consist in a method of forming a component forming a part of a breathing tube, or forming the breathing tube, comprising: extruding a tubular body from a single extrudate, the extrudate including a foaming agent for foaming of the tubular body so formed, such that, the wall of the foamed tubular body is of a sufficient minimum optical transparency that is use enables visual detection of a liquid (or condensate that may have formed) within the tubular body.

Preferably the method further comprises passing the extruded tubular body into a corrugator and forming corrugations in the extruded tubular body having a corrugation profile comprising alternating outer crests (or annular protrusions) and inner troughs (or annular recesses).

Preferably the corrugations may be of an annular corrugation or a spiral corrugation form.

Preferably the method further comprises terminating a first end with a first connector, and terminating a second end with a second connector, and wherein only one gases passageway is formed between the first connector and the second connector.

Preferably the method further comprises applying one or more of a heater or a sheath about the tubular body.

Preferably the heater is associated with a wall of the tubular body. Preferably the heater can be either associated with an interior wall surface of the tubular body or an exterior wall surface of the tubular body. Alternatively preferably, such a heater can be embedded, either partially or wholly, in the wall of the tubular body.

Preferably the component further comprises a heater. Preferably the heater is associated with a wall of the tubular body. Preferably the heater is associated with an interior wall surface of the tubular body. Preferably the heater is associated with an exterior wall surface of the tubular body. Preferably the heater is embedded, either partially or wholly, in the wall of the tubular body.

Preferably the tubular body further comprises an outer sheath. Preferably the outer sheath surrounds a heater associated with an exterior wall surface of the tubular body. Preferably the outer sheath may trap air between adjacent outer crests (or annular protrusions) and restrains a heater, such as a heater wire, associated with an exterior wall surface of the tubular body.

In a further aspect the invention consists in a component forming a part of a breathing tube, or forming the breathing tube, comprising: a tubular body having a foamed wall having a foamed wall formed from extrusion of a single extrudate, wherein the tubular body further comprises an outer sheath.

In a further aspect the invention consists in a component forming a part of a breathing tube, or forming the breathing tube, comprising: a tubular body having a foamed wall, and wherein the foamed wall is surface modified and the tubular body further comprises an outer sheath.

In a further aspect the invention consists in components as herein described with reference to any one or more of the drawings.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application and/or statements of invention, individually or collectively, and any or all combinations of any two or more said parts, elements features or statements of invention, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIG. 2A generally illustrating a lower void fraction (lower than that of FIG. 2B) of a foamed tubular body wall having greater transparency or clarity (or greater ease of visual detection of liquid within a tube); FIG. 2B generally illustrating a greater void fraction (greater than that of FIG. 2A) of a foamed tubular body wall having reduced transparency or clarity (or reduced ease of visual detection of liquid within a tube).

DETAILED DESCRIPTION OF THE PREFERRED EMBODIMENT

In the field of medical circuits, and in particular breathing circuits (including anaesthetic circuits), condensation or rain-out can be a particular problem where high humidity breathing gases come into contact with the walls of a component at a relatively lower temperature Enhancing the thermal resistance (or thermal insulation capabilities) of the walls provides benefits in this respect. However, it remains beneficial for a user or care-giver to be able to optically identify or visually discern the presence of liquid or build-up of condensate within the component. The present invention is directed toward enabling a component providing a patient and care-giver with both of these beneficial requirements.

Figure 3:
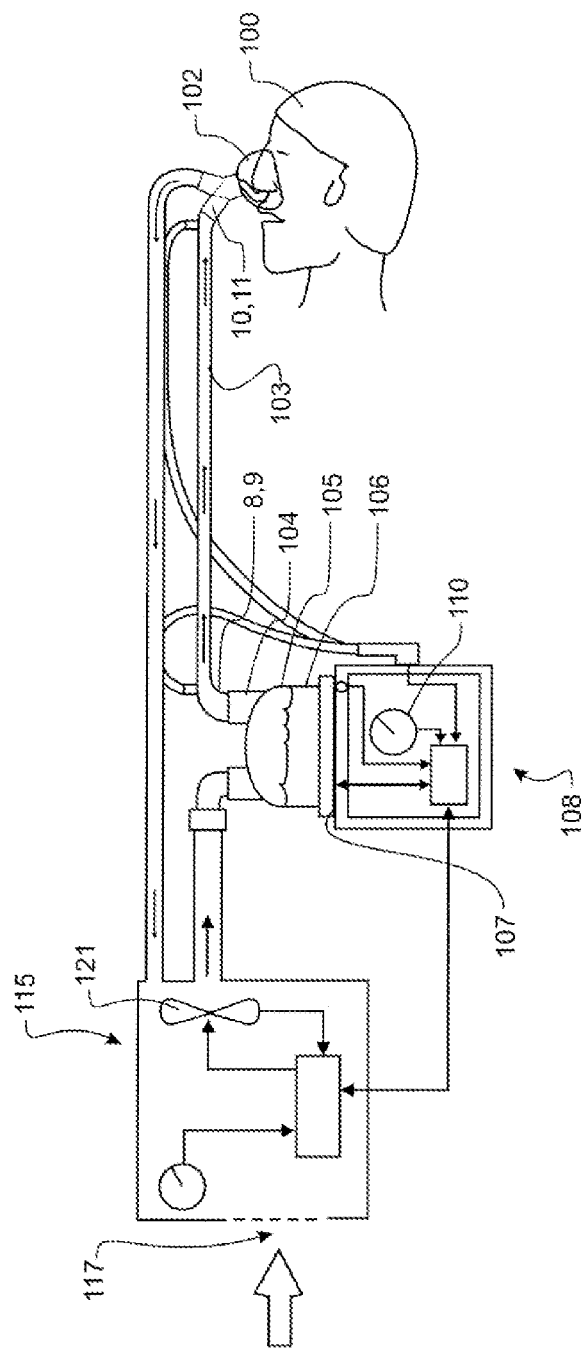
FIG. 3 is a schematic illustration of one type of breathing circuit in which a component according to the invention can be used.

With reference to FIG. 3 a humidified ventilation system is shown in which a patient 100 is receiving humidified and pressurised gases through a patient interface 102 connected to a humidified gases transportation pathway or inspiratory breathing tube 103. It should be understood that delivery systems could also be continuous, variable or bi-level positive airway pressure or numerous other forms of respiratory therapy. The inspiratory tube 103 is connected to the outlet 104 of a humidification chamber 105 which contains a volume of water 106. The inspiratory tube 103 may contain a heater or heater wires (not shown) which heat the walls of the tube to reduce condensation of humidified gases within the tube. The humidification chamber 105 is preferably formed from a plastics material and may have a highly heat conductive base (for example an aluminium base) which is in direct contact with a heater plate 107 of humidifier 108. The humidifier 108 is provided with control means or electronic controller which may comprise a microprocessor based controller executing computer software commands stored in associated memory.

In response to the user set humidity or temperature value input via dial 110, for example, and other inputs, the controller determines when (or to what level) to energise heater plate 107 to heat the water 106 within humidification chamber 105. As the volume of water within humidification chamber 105 is heated, water vapour begins to fill the volume of the chamber above the water's surface and is passed out of the humidification chamber outlet 104 with the flow of gases (for example air) provided from a gases supply means or ventilator/blower 115 which enters the chamber 105 through inlet 116. Exhaled gases from the patient's mouth are returned to the ventilator via a return expiratory breathing tube 130.

The ventilator 115 is provided with variable pressure regulating means or variable speed fan 121 which draws air or other gases through blower inlet 117. The speed of variable speed fan 121 is controlled by electronic controller 118. It will be appreciated that the patient interface 102 could equally be a nasal mask, oral mask, oronasal mask, nasal prongs or full-face mask, etc.

However, there are also other competing requirements that should be satisfied by medical tubing in the field of the present invention. For example, it is preferable that breathing tubes for breathing circuits are: resistant to crushing; resistant to restrictions in flow when bent (increased resistance to flow <50% when bent around a 1 inch cylinder); resistant to kinking; resistant to changes in length/volume under internal pressure (compliance); resistant to leaking (<25 ml/min @ 6 kPa); have low flow resistance (increase in pressure @ max. rated flow <0.2 kPa); electrically safe i.e.: sparks in the tubing can be extremely dangerous, especially in oxygen-rich environments such as oxygen therapy.

International standard ISO 5367:2000(E) (Fourth edition, Jun. 1, 2000) is one example of how some of these desirable parameters are measured and assessed, and the document is hereby incorporated into this specification in its entirety by reference. It is preferable that components of the invention meet or exceed some or all of these standards.

In this specification, terms "medical circuit" and "breathing circuit" are used to indicate the general field of the invention. It is to be understood that a "circuit" is intended to include open circuits, which do not form a complete closed circuit. For example, CPAP systems usually consist of a single inspiratory breathing tube between a blower and a patient interface. The term "breathing circuit" is intended to include such "open circuits". Similarly, the term "medical circuit" is intended to include both breathing circuits and insufflation circuits (which are also typically "open"). Similarly, the term "medical tubing" is intended to be read as flexible tubing suitable for use in the type of medical circuits described above connecting between components of a medical circuit and providing a gases pathway between components of a medical circuit.

The term "substantially uniform" wall thickness corrugated tube is intended to mean a tube having a corrugation profile wherein an outer peak, for example, comprises the maximum outside radius of the tube while also forming the maximum inner radius of the tube and an inner trough, for example, forms the minimum inner and outer radius of the tube. This type of tube is typically formed from a substantially uniform thickness extrusion that is subsequently corrugated. It will be appreciated that the subsequently formed corrugations may vary the wall thickness of the outer peak regions versus the inner trough regions of the finished tube. The ratio of minimum to maximum actual wall thickness may vary as much as 1:1.5-3.0 for example.

It will be generally understood that a "single extrudate" as used in this specification and claims means a single batch, or blend, or formulation, or mixture of material (or materials), that is fed to an extruder to be extruded. In this manner, a single layer extrusion is formed. It will be appreciated that this is in contrast to a multi-layer extrudate, such as for example those formed by co-extrusion or extrusion-coating techniques.

The phrase "visual detection" as used in this specification and claims is intended to mean recognition by human eye, for example, a person is able to visually recognise the presence, or build-up of a liquid (or condensate that may have formed) within at least a part of the tubular body. A further example includes where people are capable of visually recognising the presence or build-up of a liquid (or condensate that may have formed) in a tubular body according to this invention, when subjected to the "visual detection test method" as described herein.

Breathing Tubing

Medical tubing in the field of the present invention has a nominal bore size from approximately 10 mm to approximately 30 mm, and lengths ranging from approximately 300 mm to 2.5 m. In particular applications such as medical tubing to connect to an interface component the tubing may be significantly shorter (e.g. 50 mm to 300 mm). A catheter mount for example, may have a length of approximately 80 mm A catheter mount is a single lumen tube which in use will carry both inspiratory and expiratory breathing gases to and from a patient respectively.

Foamed Embodiment

In a first embodiment there is provided a component 1 forming a part of a breathing tube (such as for example inspiratory tube 103), or forming the breathing tube. The component 1 comprises of a tubular body 2 having a foamed wall 3 formed from extrusion of a single extrudate. The foamed wall 3 is of a sufficient minimum optical transparency such that, in use, enables visual detection of a liquid (or condensate that may have formed) within the tubular body 2.

In another embodiment however, there is provided a component 1 forming a part of a breathing tube (such as for example inspiratory tube 103), or forming the breathing tube. The component 1 comprises of a tubular body 2 having a foamed wall 3 formed from extrusion of a single extrudate. Alternatively in another embodiment, there is provided a component 1 forming a part of a breathing tube (such as for example inspiratory tube 103), or forming the breathing tube. The component 1 comprises of a tubular body 2 having a foamed wall 3, the tubular body 2 formed from a single extrudate, where the tubular body further comprises of an outer sheath 7. In both these embodiments, additional features and combinations with such embodiments are contemplated in the form of, for example, optional heating elements, external sheaths, techniques for surface modification of the tubular body's wall, including ways and amount of foaming of the wall 3, and whether the conduit is of a corrugated form or not.

In yet further embodiments however, there is provided a component 1 forming a part of a breathing tube (such as for example inspiratory tube 103), or forming the breathing tube. The component 1 can comprise of a tubular body 2 having a wall 3 with a modified surface, the tubular body formed from a single extrudate. Alternatively, in another embodiment, there is provided a component 1 forming a part of a breathing tube (such as for example inspiratory tube 103), or forming the breathing tube. The component 1 can comprises of a tubular body 2 having a wall 3 with a modified surface, the tubular body 2 formed from a single extrudate, where the tubular body further comprising of an outer sheath 7. Again, and as stated previously, in both these embodiments additional features and combinations with such embodiments are contemplated in the form of, for example, optional heating elements, external sheaths, techniques for surface modification of the tubular body's wall, including ways and amount of foaming of the wall 3, and whether the conduit is of a corrugated form or not.

Figure 2A:
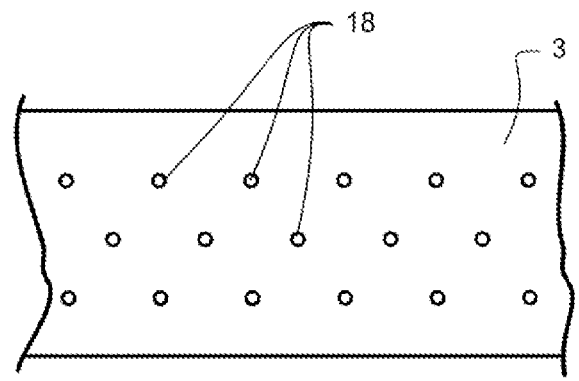
FIGS. 2A and 2B are section views through a wall section of a tube generally illustrating different void fractions generated by foaming.
Figure 2B:
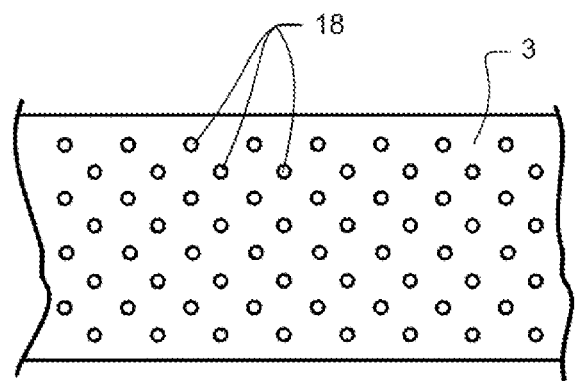

FIGS. 2A and 2B generally illustrate foamed tubular body wall sectional views. FIG. 2A illustrates a wall section having a void fraction less than the void fraction of the wall in FIG. 2B. The void fraction helping to improve insulator capabilities of the component 1. Voids are shown as gas bubbles or foamed voids 18.

FIG. 2A generally illustrates a wall having an optical clarity sufficient to enable visual detection of a liquid or condensate that may have built-up within the tubular body 2 of such a component 1. Such optical characteristics allows a user or care-giver to visually discern the presence of liquid within the tubular body, and if necessary, take action to drain the liquid from the component, or taker other necessary action. Or, at least allow maintenance to be undertaken.

In contrast, although not specific to the illustration of FIG. 2B, FIG. 2B generally illustrates that the greater the level of void fraction, the greater the likelihood of opacity or reduced optical clarity or transparency through the wall of the tubular body 2. The void fraction of the wall should be at least of a level that allows a minimum of transparency for optical detection by a user or care-giver of a patient using such a tubular body (or component 1).

Figure 1:
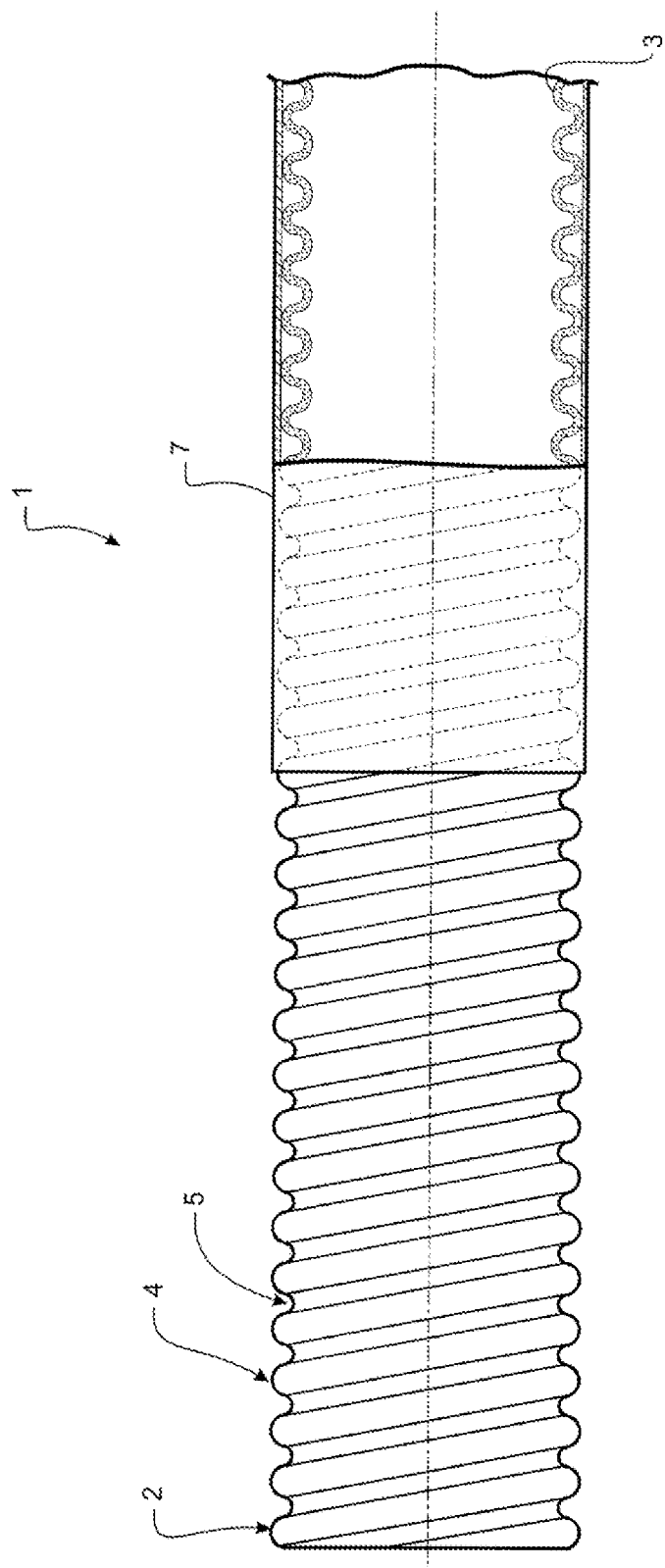
FIG. 1 illustrates a section of a corrugated tubular component, including a partial cut-away side view of a medical tube component according to one embodiment of the invention, for example a breathing tube or a limb of an insufflation system, optionally including the sheath shown on a part of the tube component.

The wall 3 of such a tubular body 2 can be optionally corrugated, or of a corrugate profile (for example as shown in FIG. 1). For example, the corrugation profile can comprise of alternating outer crests 4 (or annular protrusions) and inner troughs 5 (or annular recesses). The outer crests 4 can correspond to a location of maximum inner radius and maximum outer radius of the tubular body, and the inner troughs 5 can correspond to a location of minimum inner radius and minimum outer radius of the tubular body. Such corrugations may be of an annular corrugation or spiral corrugation form. Alternatively, the tubular body may be of a smooth or non-corrugate profile.

The tubular body 2 advantageously has a substantially uniform wall thickness. A wall thickness of about 0.2 mm to about 1 mm, or about 0.3 mm to about 0.9 mm, or about 0.4 mm to about 0.8 mm, or about 0.5 mm to about 0.7 mm, or about 0.3 mm to about 0.6 mm, or about 0.4 mm to about 0.7 mm. The wall may be about 0.2, 0.3, 0.4, 0.5, 0.6, 0.7, 0.8, 0.9 or 1 mm thick.

Such a foamed wall 3 preferably provides a level of thermal insulative of, at least, the interior (or gas flow passage) of the tubular body 2 bounded by the foamed wall 3. In particular, the wall 3 is thermally insulative of the contents (such as for example humidified gases flowing through the gas flow passage) of the tubular body 2 to the potential cooling effects of the environment surrounding the tubular body (for example, insulating from the ambient air surrounding a breathing circuit, or a laparoscopic insufflation system). The environment surrounding the component or tubular body 2 is for example, a hospital ward or room, an operating theatre, or other locations where the patient may be located.

The foamed wall 3 is a single-piece of a foamed polymer material, for example being formed by extrusion of a single extrudate.

Foaming of the tubular body's wall 3 allows enhanced thermal insulative properties of the component as part of a breathing tube or breathing circuit, for example. More specifically, the foamed wall 3 may provide for overall increased thermal insulative properties of the component, particularly of, at least, the interior of the tubular body bounded by the foamed wall. In various embodiments the foamed wall 3 has or provides for a thermal conductivity of about 0.2 to about 0.4 W/m–° K (Watt per meter Kelvin). It will however be appreciated the foamed wall 3 may beneficially provide for other levels of thermal conductivity, advantageously thermal conductivities of about 0.15 to 0.35 W/m–° K or of about 0.25 to 0.45 W/m–° K are preferred.

As part of foaming the wall of the tubular body 2, the foaming provides for certain gas voids 18 within the wall 3. A quantitative measure of the gas voids 18 can be expressed as a void fraction. A void fraction is indicative of the volume of void (gas) space occupying a unit volume of the tubular body.

The gas voids 18 may assist in contributing to the insulation performance of the component 1, in addition to enabling the desired level of tubular wall transparency.

A minimum level of transparency of the tubular wall 2 enables the visual detection of liquid (or condensate that may have built-up within the tubular body or component) by a person.

Various levels of void fraction can be of up to about 10%, or up to about 9%, or up to about 8%, or up to about 7%, or up to about 6% or up to about 5%, or up to about 4%, or up to about 3%, or up to about 2%, or up to about 1%, or ranges of void fractions of the tubular body's wall of about 1%, of about 1.5%, of about 2%, of about 2.5%, of about 3%, of about 3.5%, of about 4%, or about 4.5%, or about 5%, or about 5.5%, or about 6%, or about 6.5%, or about 7%, or about 7.5%, or about 8%, or about 8.5%, or about 9%, or about 9.5%, or about 10%.

According to the applicant's test results, the most preferred void fractions to be formed in a tubular body's wall is about 5.5% or about 7.5%, or is about 5.5% to about 7.5%. Such void fractions enable a person to optically identify or visually discern the presence of liquid, accumulated liquid or other build-up of condensate (for example as a result of rain-out).

The tubular body's foamed wall 3 can be foamed either by physical foaming techniques, or by chemical foaming techniques, or by a combination of both of these.

The extrudate may comprise of a number of polymer materials to which other materials may be added (for example by blending as or to form a master batch). Preferred materials include one or more polymer(s) of Linear Low Density Polyethylene (LLDPE), Low Density Polyethylene (LDPE), Polypropylene (PP), Polyolefin Plastomer (POP), Ethylene Vinyl Acetate (EVA) or blends of these materials.

Plasticised PVC may also be a suitable material, but it is not as well accepted for environmental reasons.

The polymer material can comprises at least about 98.4, 98.5, 98.6, 98.7, 98.8, 98.9, 99.0, 99.1, 99.2, 99.3, 99.4, 99.5, 99.6, 99.7, 99.8, or 99.9 weight percent (wt. %) of the total extrudate. In particular embodiments the polymer material comprises about 99.49 wt. % of the total extrudate (as LLDPE).

Alternatively preferably the polymer comprises about 99.488 wt. % of the total extrudate.

Surface Modification

One such additional material that can be included with the extrudate is one or more surface modification agents.

A surface modification agent may preferably comprise glycerol monostearate (GMS), ethoxylated amine, alkanesulphonate sodium salt, or lauric diethanolamide.

Preferably the surface modification agent comprises at least about 0.05, 0.1, 0.15, 0.2, 0.25, 0.3, 0.35, 0.4, 0.45, 0.5, 1.1, 1.2, 1.3, 1.4, or 1.5 weight percent (wt. %) of the total extrudate. More preferably the surface modification agent comprises about 0.25 wt. % of the total extrudate. Alternatively preferably the surface modification agent comprises about 0.5 wt. % of the total extrudate.

For example, MLDNA-418 supplied by Clariant (New Zealand) Ltd. and under the product name "418 LD Masterbatch Antistatic" is a surface modification agent master batch with 5(±0.25)% glycerol monostearate (CAS No. 123-94-4) as an active ingredient.

A surface modification agent may additionally be included in the extrudate. Such an agent assists in increasing the surface energy (or the wettability) of the surface of the formed component or tube. In this manner, advantageously increasing the surface energy may act to promote reduced contact angles between drops or beads of condensate or liquid that may build up on the surface.

The contact angle is the angle formed by the solid surface of the component or tube wall and the tangent line to the upper surface at the end point of a liquid droplet. Contact angle measurement is a non-destructive method of determining the wetting behaviour of liquids on a solid surface. It enables the calculation of surface and interfacial tension along with spreading coefficients. The surface tension calculated from the contact angle data are a characteristic measurement for the respective surface and fluid system.

The contact angle between a liquid and a surface is measured using a goniometer (angle measurement device). A precise volume of the liquid is dispensed on the cleaned and dried flat test surface using a precision syringe. The droplet is allowed to stabilize for a few seconds and a high magnification camera is used to capture the image of the droplet. The image is digitised and the angle between the test surface and the tangent line along the droplet surface is measured.

Reducing contact angle increases contact area between the droplet and solid surface, and also reduces droplet thickness, enhancing heat conduction through the droplet. Both effects increase droplet evaporation rate.

Increasing the energy of a surface reduces contact angle of a droplet placed on the surface. In this manner, a droplet of liquid on the surface of a higher energy surface can preferentially have a greater surface area in contact with the surface, then a surface of relatively lower energy.

Advantageously, the droplet may be spread across a larger surface area of the surface and, therefore, be more likely to re-evaporate into the gas stream flowing through the component or tube.

For example, the droplet or bead may spread across the internal surface of the tube's wall, allowing greater surface area for re-evaporation into the passing gas stream.

In another example, where the tube is corrugated (whether as an annular corrugate or spiral corrugate form), the droplet or bead of water is more likely to form in a part of the corrugation of low temperature position (i.e. generally this is a part of the corrugation closest to or most exposed to ambient conditions surrounding the tube). In such a case, altering the surface properties of the tube surface can promote a droplet or bead formed at the low temperature position to spread across the tube surface and in doing so may move towards a region of warmer temperature. Such migration of movement of the droplet or bead can allow for further improved re-evaporation rates, both due to the droplet possibly moving toward regions of warmer temperatures, as well as possibly toward regions of the tube which are exposed to greater or faster gas stream flows. Greater re-evaporation rates may therefore be achieved by providing for improved migration of a droplet or bead radially inward from the internal surface wall of the tube.

In respect of surface modification, it should be appreciated that in various aspects of the invention, a component 1 and its tubular body 2 can be formed from a single extrudate where the body 2 has a modified surface. Modified surfaces may preferably facilitate the advantages of re-evaporation rates or droplet migration as described above.

Some of the other methods which may be used to increase surface energy include:

Physical
Physical adsorption
Langmuir-Blodgett film
Chemical
Oxidation by strong acids
  Ozone treatment
  Chemisorption Flame treatment
Radiation
  Plasma (glow discharge)
  Corona discharge
  Photo-activation (UV)
  Laser
  Ion beam
  Electron beam
  γ-irradiation A chemical additive or agent can also be used to impart the increase in surface energy and wettability to the component or tube so formed.

Such a surface modification agent may for example be glycerol monostearate, a food grade emulsifier.

TABLE 1

Contact angle measurements for samples of LLDPE with different surface treatments

| Description of Surface | Liquid | Average Contact Angle (degrees) |
|---|---|---|
| Linear Low-density Polyethylene (LLDPE), as manufactured | Water | 97.39 |
| Linear Low-density Polyethylene (LLDPE), fluorinated, washed | Water | 67.56 |
| Linear Low-density Polyethylene (LLDPE), plasma-treated, 10% O2, 300 Watts, 30 seconds | Water | 44.98 |
| Linear Low-density Polyethylene (LLDPE), with 5% MLDNA-418 as surface modification agent additive | Water | 33.09 |

The sample with 5% MLDNA-418 surface modification agent produced the lowest measured contact angle compared to other surface modification methods tested.

In Table 1 above and where referenced elsewhere in this specification, contact angle measurements were based on static drop shape testing methods conducted in accordance with ASTM Standard D7334, 2008, "Standard Practice for Surface Wettability of Coatings, Substrates and Pigments by Advancing Contact Angle Measurement".

Modifying the surface properties of the tubular body 2 (i.e. the foamed wall 3 of the resultant tubular body) enables variation of the surface property contact angles.

By choosing various surface modification methods, it is possible to provide a foamed wall 3 having surface property contact angles of less than about 50, 45, 40, 35, 30, 25, 20 degrees (°), as measurable by an angle measurement device such as a geniometer. Advantageously, foamed walls 3 of a resultant tubular body enabling surface property contact angles of less than about 35° appear to provide useful results.

Foaming

Another additional material to be included with the extrudate is one or more chemical foaming agents.

A chemical foaming agent enables foaming of the extrudate material as part or after the extrusion process.

For example, the chemical foaming agent can comprise at least about 0.005, 0.006, 0.007, 0.008, 0.009, 0.01, 0.011, 0.012, 0.013, 0.014, 0.015, 0.016, 0.017, 0.018, 0.019, or 0.02 weight percent (wt. %) of the total extrudate.

In preferred embodiments, the chemical foaming agent can comprise about 0.01 wt. % to about 0.012 wt. % of the total extrudate.

As part of a chemical foaming extrusion process, the polymer resin component of an extrudate is mixed with a chemical foaming agent. Chemical foaming agents are sometimes also referred to as blowing agents.

Some preferred chemical foaming agents include those that comprise calcium oxide. For example, MHYNA-CF20E supplied by Clariant (New Zealand) Ltd. under the product name Hydrocerol CF20E is a chemical foaming agent in the form of a blowing agent master batch with about 0.5-1% calcium oxide as an active ingredient.

During a chemical foam extrusion process the polymer resin component and chemical foaming agent(s) are mixed and melted. The chemical foaming agent(s) decomposes and liberates gas which is dispersed in the polymer (or master batch or extrudate) melt and which expands upon exiting the die of an extruder.

It will also be appreciated other foaming techniques can be employed for the forming of a foamed wall 3 of the component 1 or tube, such as by physical rather than chemical foaming methods. Physical foaming methods would include gas being introduced directly into the melt or extrudate while under pressure. As the melt or extrudate is then extruded the pressure is reduced allowing the gas to expand. For example, one such physical foaming technique includes blowing or injecting of gas(es) into extrudate at or near the point of extrusion. Such gas(es) may include nitrogen, carbon dioxide, pentane or butane.

Heaters and Sheaths

Figure 4:
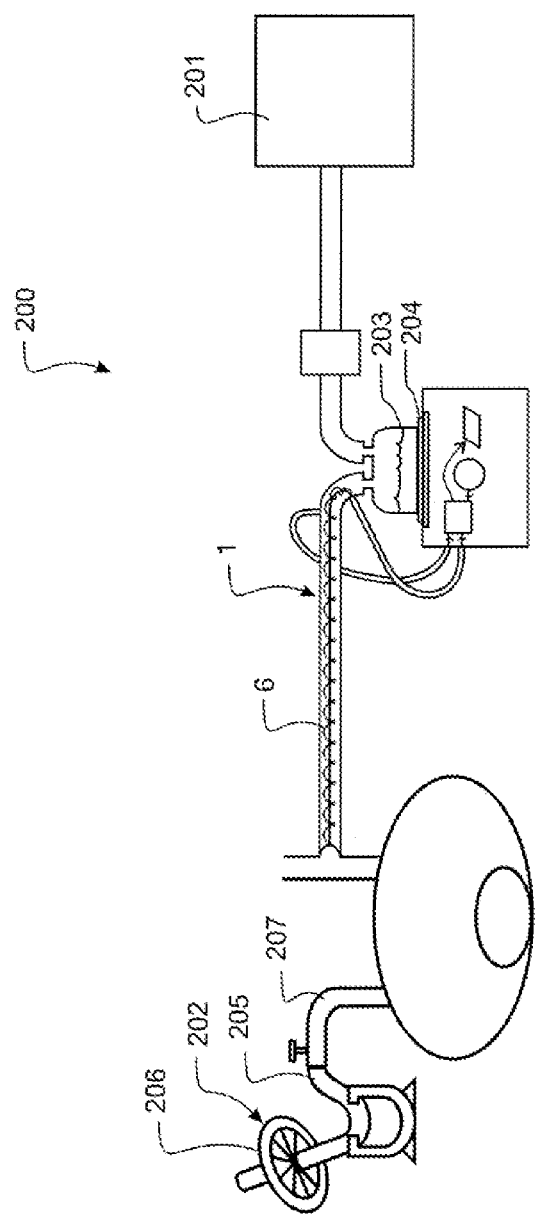
FIG. 4 is a schematic illustration of a patient and a humidified insufflation system showing the inlet and exhaust limbs.
Figure 7:
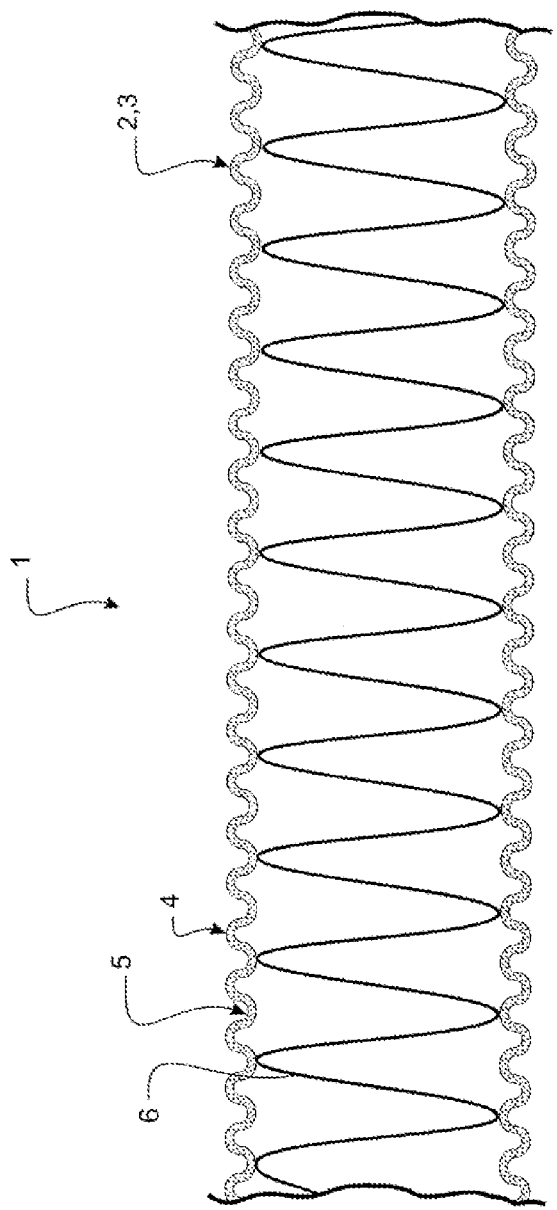
FIG. 7 is a generalised view of a foamed tubular body according to one embodiment of the invention incorporating a heater wire within the passageway of the tubular body.
Figure 8:
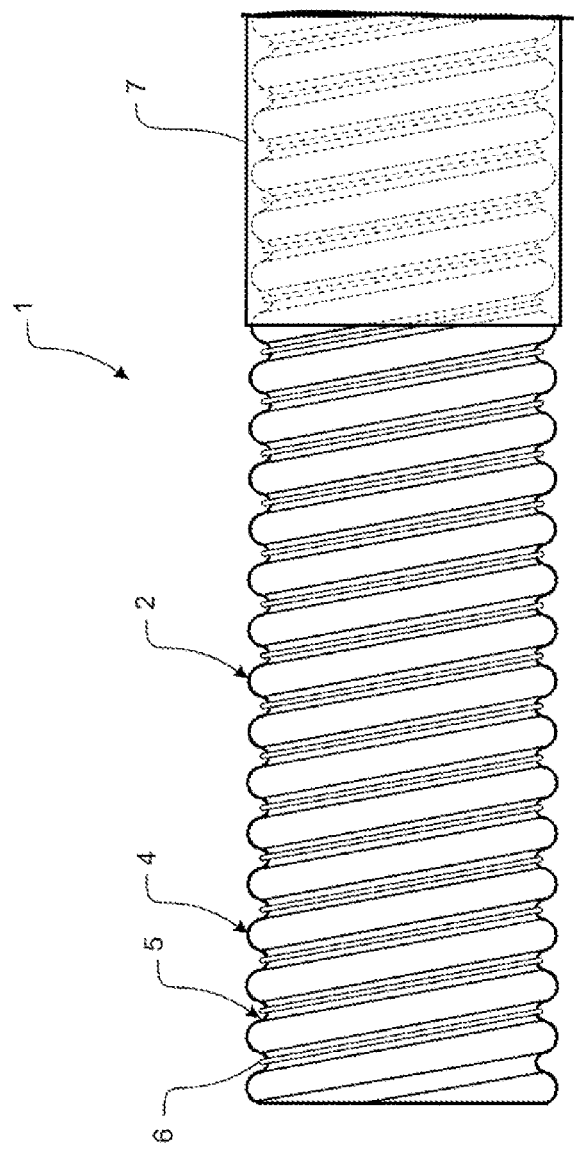
FIG. 8 is a generalised view of a foamed tubular body according to one embodiment of the invention incorporating a heater wire located about the external surface of the tubular body's outer wall surface.

The component 1 can optionally further include a heater 6 (as shown for example in FIGS. 4, 7, 8).

The heater can be associated with a wall of the tubular body, for example an interior wall surface (such as FIGS. 4, 7) or an exterior wall surface (such as FIG. 8) of the tubular body.

In other embodiments, the heater can be embedded, either partially or wholly, in the wall 3 of the tubular body 2 (not shown).

In yet a further embodiment, the tubular body 2 can optionally include an outer sheath 7. Such an outer sheath 7 surrounds the tubular body 2.

Where a heater is associated with an exterior surface of the tubular body 2, the sheath 7 would additionally surround or envelope the heater.

However, it is also contemplated that in various aspects of the invention an outer sheath 7 may surround the component 1, whether a heater is included with the tubular body 2 or not.

The sheath 7 is contemplated as being provided in various forms. For example, the sheath 7 may be applied about the tubular body 2 as an extruded outer layer, as a wrapping about the body 2, or as a sleeve that is slid or pulled into position about the tubular body 2. Such a sheath 7 may be formed of similar materials as the tubular body 2, for example LLDPE (low low density polyethylene). The sheath 7 may assist in further improving thermal performance of the tubular body 2. The sheath 7 may be of any necessary thickness, although thickness and the material used should be balanced with the need to maintain flexibility of the tubular body 2.

In one embodiment it is contemplated an outer sheath 7 may have a wall thickness of about 100 micrometres.

Where an outer sheath 7 is extruded about the tubular body 2, for example, such an extrusion could be a sequential step to initial extrusion of the tubular body 2, that is, an extrusion step post-formation of the body 2. Further, where an outer sheath 7, for example, is a wrap about the body 2, the sheath 7 may be of a tape or ribbon form and can be spirally wound about the length of the body 2. Still further, where an outer sheath 7 is pre-formed as a hollow tube, it may be sleeved into position about the outside of the body 2.

Where a heater 6 is employed however, the heater 6 can be of a heater wire form. Materials for such heater wires are copper, aluminium or a PTC (positive temperature coefficient) type material. Aluminium is not as conductive as copper, but may be an economical choice even though the wire diameter is larger for the same resistance. While the applied circuit voltage is intrinsically safe (less than 50V), for corrosion resistance and best electrical safety in the event of the tube or sheath being damaged, the wire will ideally be self insulated, either by enamel coating or anodising in the case of aluminium. Alternatively an extruded plastic sheath can be fitted about the heater wire.

Further advantageously, the outer sheath 7 may trap air between adjacent outer crests 4 (or annular protrusions). This may assist in further insulation of the gas passing through passage of the component 1. Where for example a heater 6 is employed with the component 1 and an outer sheath is also used, the outer sheath 7 can help to restrain the heater 6, such as a heater wire, in position when the heater is associated with an exterior wall surface of the tubular body.

Where the component 1 is a breathing tube, or a part of a breathing tube, it can be terminated by a first connector 8 at an inlet 9 and a second connector 10 at an outlet 11 (for example as shown in FIG. 3). In this manner, only one gases passageway is provided the length between the inlet connector and the outlet connector.

In other contemplated forms, the component 1 with its tubular body 2 can form a part or further component of a conduit for use in at least part of an insufflation system (for example such as that shown in FIG. 4). In addition, the component 1 with its tubular body 2 can alternatively form a part of or a further component of a breathing tube for use in a breathing circuit (for example such as that shown in FIG. 3).

Foamed Heater Embodiment

In another embodiment there is provided a component 1 forming a part of a breathing tube, or forming the breathing tube (such as for example as illustrated in FIG. 3 or 4). Such a component 1 comprises of a tubular body 2 having a foamed wall 3 formed from a single extrudate, and including a heater 6 therein.

The foamed wall 3 is of a sufficient minimum optical transparency that, in use, enables visual detection of a liquid (or condensate that may have formed) within the tubular body 2.

The details for such a further embodiment are similar to that previously described in the first embodiment above.

Reference can also be made to FIGS. 7 and 8 generally illustrating a tubular body including a heater 6, such as a heater wire.

FIG. 7 illustrates the placement of a heater wire within the internal passageway of the tubular body, while FIG. 8 illustrates the placement of a heater wire about the external surface of the tubular body's wall.

More particularly, with this embodiment the heater 6 is associated with a foamed wall 3 of the tubular body 2.

It will be appreciated there are various forms in which the heater 6 can be associated with a wall of the tubular body as previously discussed.

In a further option, the tubular body 2 may optionally be surrounded by an outer sheath 7, the operation and benefits of which are previously discussed. The outer sheath 7 may be employed, whether or not a heater 6 is also included.

In both the embodiments described above, such a method of forming a component 1 forming a part of a breathing tube, or forming the breathing tube, comprises extruding a tubular body from a single extrudate. The single extrudate including a foaming agent for foaming of the tubular body so formed, such that, the wall 3 of the foamed tubular body 2 is of a sufficient minimum optical transparency that is use enables visual detection of a liquid (or condensate that may have formed) within the tubular body 2.

In one such embodiment, the method comprises passing the formed extruded tubular body 2 into a corrugator and forming corrugations along the extruded tubular body having a corrugation profile comprising alternating outer crests 4 (or annular protrusions) and inner troughs 5 (or annular recesses). The corrugator may form annular or spiral corrugations.

In one embodiment of the invention, the component forming a part of a breathing tube, or forming a breathing tube, is formed according to the steps of i) mixing or providing of a master batch of extrudate material (i.e. material for extrusion), ii) feeding the master batch to an extrusion die head, iii) extruding the extrudate into a tubular body for the component. Optionally, the tubular body is further fed into a corrugator for forming of corrugations.

Such a master batch can be provided with a chemical foaming agent included, and optionally a chemical surface modification agent may be included (although it will be appreciated other forms of surface modification agent techniques may be used, for example the physical techniques as described herein).

In one example, the process used to make such a component involves extruding a molten tubular profile into a corrugator machine utilising an endless chain of mould blocks to form a flexible corrugated tube.

An extruder such as a Welex extruder equipped with a 30-40 mm diameter screw and typically a 12-16 mm annular die head with gap of 0.5-1.0 mm has been found to be suitable for producing low cost tubes quickly. Similar extrusion machines are provided by American Kuhne (Germany), AXON AB Plastics Machinery (Sweden), AMUT (Italy), Battenfeld (Germany and China).

A corrugator such as those manufactured and supplied by Unicor® (Hassfurt, Germany) has been found to be suitable for the corrugation step. Similar machines are provided by OLMAS (Carate Brianza, Italy), Qingdao HUASU Machinery Fabricate Co., Ltd (Qingdao Jiaozhou City, P.R. China), or Top Industry (Chengdu) Co., Ltd. (Chengdu, P.R. of China).

Figure 6:
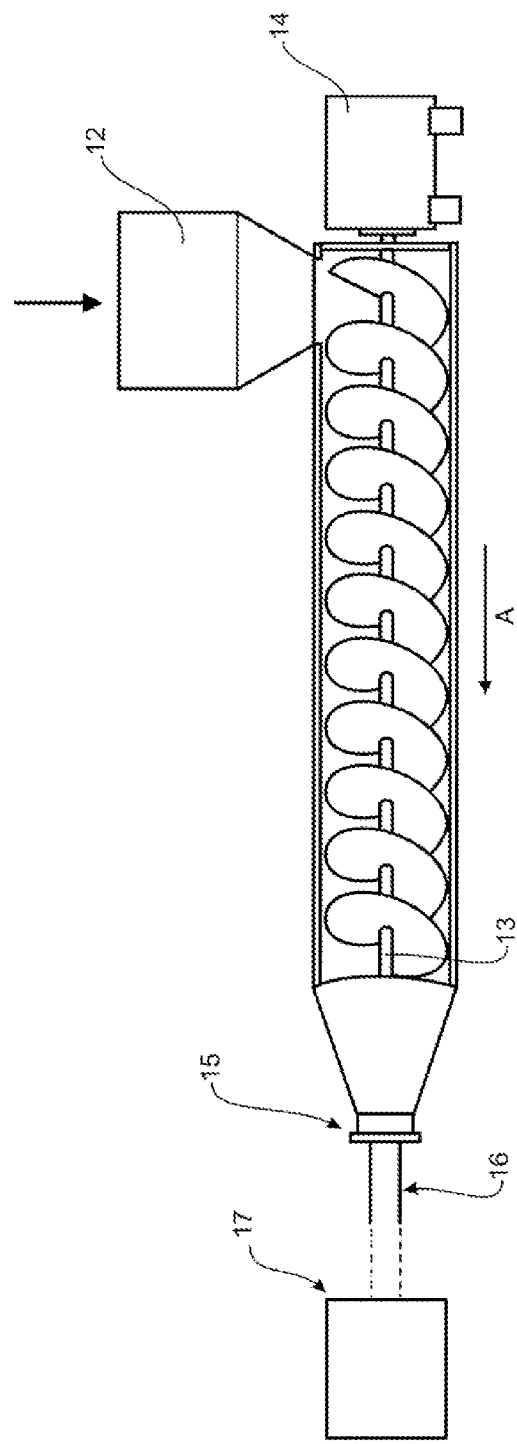
FIG. 6 is a schematic illustration of a further preferred forming method for medical tubing, including hopper feed, screw feeder to a die head, and terminating with a corrugator.

FIG. 6 generally illustrates a further setup where there is provided a feed hopper 12 for receiving raw ingredients or material (e.g. master batch and other materials) to be passed through a screw feeder 13 driven by a motor 14 in direction A toward a die head 15. The molten tube 16 is extruded out of the die head 15, and can be optionally then fed to a corrugator 17 of the type as described above.

During manufacture, the molten tube 16 is passed between a series of rotating moulds/blocks on the corrugator after exiting the extruder die head 15 and is formed into a corrugated tube such as that illustrated in FIGS. 1, 7 and 8 for example.

The molten tube is formed by vacuum applied to the outside of the tube via slots and channels through the blocks and/or pressure applied internally to the tube via an air channel through the centre of the extruder die core pin. If internal pressure is applied, a specially shaped long internal rod extending from the die core pin and fitting closely with the inside of the corrugations may be required to prevent air pressure escaping endways along the tube.

The tube 1 has a wall 3 that is preferably between approximately 0.3-1 mm thick for a breathing tube of typical dimensions (i.e. between approximately 10 mm and 30 mm diameter for neonatal and adult applications respectively and approximately 1-2 meters in length).

Such a component according to this invention may also include includes a plain cuff region for connection to an end connector fitting.

Similarly, the end connector fitting of the present tube is preferably of a standard type (moulded plastic) according to the intended use of the medical tubing and may preferably be permanently fixed and/or air tight by friction fit, adhesive bonding, over moulding, or by thermal or ultrasonic welding etc. For example, the end connector may incorporate an internal medical taper.

Figure 5:
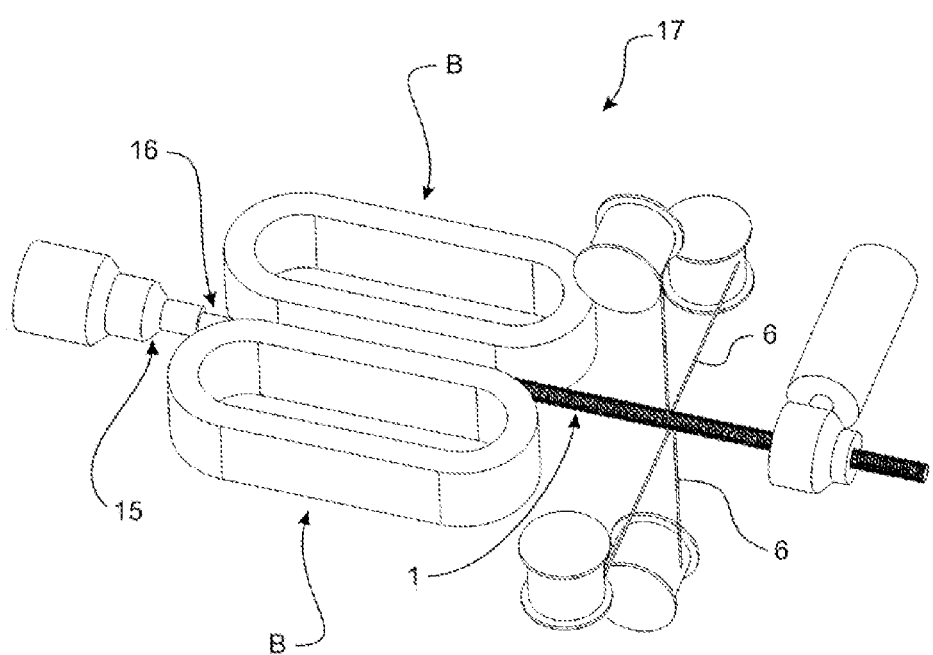
FIG. 5 is a schematic illustration of one preferred forming method for medical tubing.

One advantage of the preferred type of component or tube manufacture described above with reference to FIG. 5 is that some of the mould blocks B can include end cuff features that are formed at the same time as the tubular component 1. Shown is a molten extruded tube 16 exiting the die 15 of an extruder before passing into a corrugator 17. On exiting the corrugator 17, a heater wire 6 is wound about the exterior of the formed tubular component.

Manufacture speeds can be significantly increased by the reduction in complexity and elimination of secondary manufacturing processes. While this method is an improvement over separate cuff forming processes, a disadvantage of the prior art plain cuff is that the corrugator must slow down to allow the wall thickness of the tube in this area to increase (the extruder continues at the same speed).

The cuff thickness is increased to achieve added hoop strength and sealing properties with the cuff adaptor fitting.

Further, the heat of the molten polymer in this thicker region is difficult to remove during the limited contact time with the corrugator blocks and this can become an important limiting factor on the maximum running speed of the tube production line.

Condensate Accumulation Test—Performance Results

Test Method

The test circuit is laid horizontally inside a wind or convection tunnel. Air flow inside the tunnel is set to about 0.5 m/s and the room ambient temperature is maintained at about 18° C. which is at the lower-end recommended use temperature for the humidifier. The tube is connected to a humidification chamber that delivers moisture-saturated (i.e. >95% RH) air at 37° C.

Condensate is allowed to accumulate inside the tube and the weight gained by the tube in 16 hours is recorded as the accumulated condensate.

Condensate Test Experimental Results

TABLE 2

Condensate accumulation in breathing tube samples with different additive concentrations

| Sample Description | Condensate Accumulation in 16 hours (grams) | Reduction versus current product (%) |
|---|---|---|
| Current product Linear Low-density Polyethylene (LLDPE) | 127.18 | — |
| Linear Low-density Polyethylene (LLDPE) With 5% MLDNA-418 Surface Modification Agent | 115.98 | 9 |
| Linear Low-density Polyethylene (LLDPE) With 10% MLDNA-418 Surface Modification Agent | 105.34 | 17 |
| Linear Low-density Polyethylene (LLDPE) With 1.0% CF20E Foaming Agent | 118.11 | 7 |

TABLE 2-continued

Condensate accumulation in breathing tube samples with different additive concentrations

| Sample Description | Condensate Accumulation in 16 hours (grams) | Reduction versus current product (%) |
|---|---|---|
| Linear Low-density Polyethylene (LLDPE) With 1.2% CF20E Foaming Agent | 114.93 | 10 |
| Linear Low-density Polyethylene (LLDPE) With 5% MLDNA-418 Surface Modification Agent and 1.0% CF20E Foaming Agent | 90.1 | 29 |
| Linear Low-density Polyethylene (LLDPE) With 5% MLDNA-418 Surface Modification Agent and 1.2% CF20E Foaming Agent | 83.16 | 35 |

Trends indicate that increasing surface modification agent content increases the impact of surface modification in condensate accumulation inside the tube. Results indicate that the benefit from foaming and surface modification in reducing condensate is more than a linear accumulation. It appears there are synergistic benefits from the combination of foaming agent with a surface modification agent. Foaming agents produce air bubbles inside the tube during extrusion. Air has a very low thermal conductivity which causes a significant increase in the thermal insulation property of the tube.

From these results, it is apparent that small variations in the composition of the mix will have a significant impact to performance.

Visual Detection Test Method

Six (6) polyethylene breathing tube samples (corrugated, 22 mm diameter and 1.5 meter long) having MHYNA-CF20E foaming agent concentrations of 0%, 1%, 1.2%, 1.5% and 1.8%, and 2.0% were assembled using standard breathing circuit heater wires and connectors. A precision syringe was used to inject 100 mL of clean deionized water in each of the tubes. Air was allowed to pass through the test breathing tubes from a portable ventilator.

The tubes with 0% (current state-of-the-art) and 2% MHYNA-CF20E (foaming agent master batch) were used as references to represent the extreme ends of the transparency range to be evaluated, where for example, 0% having an acceptable water detectability (Reference A) and 2% MHYNA-CF20E having no water detectability at all (Reference B).

Ten (10) volunteer participants with varying age, ethnicity and gender were asked to conduct a visual inspection of the tubes and evaluate the ease with which they detected water inside the tube compared to the reference tubes in a scale of 1 to 5, as per the following guideline:

Water detectability is as good as in Reference A
Water is detectable but not as good as in Reference A
Water is reasonably detectable
Water is barely detectable but not as bad as Reference B
Water is as undetectable as in Reference B Nine (9) out of ten (10) participants rated the tube with 1.2% MHYNA-CF20E as having reasonable water detectability with an average score of 3. On the other hand, the tube with 1% MHYNA-CF20E scored an average of 2. 10 out of 10 participants considered the tube as having reasonable or better water detectability than the rest of the test samples except Reference A. Results of the study showed that the 1.5% and 1.8% MHYNA-CF20E (greater than 10% foam/void fraction) have unacceptable amount of foaming with 10 out of 10 indicating that the two tubes have very poor water detectability.

Further Performance Results

Table 3 sets out comparative data between reference samples of 100% LLDPE corrugate tubes (see reference samples 1, 2, 3) against corrugated tubes of similar dimensions formed with a polymer material of LLDPE plus other materials. Reference sample 1 is the current state-of-the art having a 100% LLDPE corrugate tube and an internal coiled heater. Reference sample 2 is a 100% LLDPE tube with an internal coiled heater and outer sheath of polyethylene. Reference sample 3 has a 100% LLDPE tube with an external filament heater and outer polyethylene sheath.

As shown, the various comparative corrugate tube forms comprises LLDPE as a polymers material plus a chemical foaming agent (examples 1, 2, 3), LLDPE plus a chemical surface modification agent (examples 4, 5, 6, 7), and LLDPE plus a combination of a chemical foaming agent and a chemical surface modification agent (examples 9, 10, 11, 12).

The examples exemplify the performance of the various tubes in respect of their condensate accumulation test results (test procedure being the same as the data obtained in Table 2). Notably, the results for examples 9-12 provide significant improvement over the reference samples in terms of reduction in accumulated condensation.

The examples also exemplify the surface modification achieved by including a chemical surface modification agent within the extrudate. Notably, the surface property contact angle (for water) was altered from about 97° in the reference samples to about 33° in the examples using a surface modification agent.

Further, there are unexpected improvements in the condensate accumulation test results for examples 9-12. The foaming of the wall and alteration of surface properties of the wall surface provide for improved condensate accumulation results over the reference samples. Those improvements are not a linearly cumulative of the benefits that appear provided by either foaming or surface modification on their own. Such non-linear accumulation of performance indicates the synergistic benefits of such combination.

It is believed the particular improvements are resultant from the combination of increased void fraction in the tube wall (i.e. about 5.5% to 7.5% void fraction) due to foaming (and therefore thermal resistance to heat losses from warm gases passing through the tube), and possibly enhanced re-evaporation rates of condensate or other liquid build-up in the tube due to reduced surface property contact angle for liquid on the wall surface within the tube.

Addition of an outer sheath to an extruded 100% LLDPE tube reduced condensate accumulation by 26.7%. Furthermore, external filament heating of a 100% LLDPE tube reduced condensate accumulation by 53.1%. Externally heating a surface modified tube that has not been foamed did not give any condensate reduction benefits. On the other hand, externally heating a foamed conduit (without surface modification) gave about a further 4.6% condensate reduction.

However, external filament heating of a foamed and surface-modified breathing tube gave a 27.8% less condensate compared to a similarly externally heated 100% LLDPE tube. This further demonstrates the synergistic benefit from the combination of foaming and surface-modification in minimizing condensate accumulation inside a humidified breathing circuit.

| Tube examples | Base material (X wt. % of extrudate) | Foaming agent (wt. % of total extrudate) | Surface modification agent (wt. % of total extrudate) | Wall thickness (mm) | Void fraction of tube (%) | Tube wall thermal conductivity (W/m °K) | Surface Property Contact Angle (degrees) |
|---|---|---|---|---|---|---|---|
| Reference sample 1 | 100% LLDPE | (0%) | (0%) | Crest - 0.3 Trough - 0.6 | 0 | 0.4 | 97 |
| Reference sample 2 | 100% LLDPE | (0%) | (0%) | Crest - 0.3 Trough - 0.6 | 0 | 0.4 | 97 |
| Reference sample 3 | 100% LLDPE | (0%) | (0%) | Crest - 0.3 Trough - 0.6 | 0 | 0.4 | 97 |
| Example 1 | 99.99% LLDPE | Calcium oxide (0.01%) | (0%) | Crest- 0.4 Trough- 0.7 | 5.5 | 0.3 | 97 |
| Example 2 | 99.988% LLDPE | Calcium oxide (0.012%) | (0%) | Crest- 0.5 Trough- 0.7 | 7.5 | 0.3 | 97 |
| Example 3 | 99.988% LLDPE | Calcium oxide (0.012%) | (0%) | Crest- 0.5 Trough- 0.7 | 7.5 | 0.3 | 97 |
| Example 4 | 99.5% LLDPE | (0%) | Glycerol monostearate (0.25%) | Crest - 0.3 Trough - 0.6 | 0 | 0.3 | 33 |
| Example 5 | 99.0% LLDPE | (0%) | Glycerol monostearate (0.5%) | Crest - 0.3 Trough - 0.6 | 0 | 0.3 | 30 |
| Example 6 | 99.5% LLDPE | (0%) | Glycerol monostearate (0.25%) | Crest - 0.3 Trough - 0.6 | 0 | 0.3 | 33 |
| Example 7 | 99.5% LLDPE | (0%) | Glycerol monostearate (0.25%) | Crest - 0.3 Trough - 0.6 | 0 | 0.3 | 33 |
| Example 8 | 99.0% LLDPE | 0%) | Glycerol monostearate (0.5%) | Crest - 0.3 Trough - 0.6 | 0 | 0.3 | 33 |
| Example 9 | 99.49% LLDPE | Calcium oxide (0.01%) | Glycerol monostearate (0.25%) | Crest- 0.4 Trough- 0.7 | 5.5 | 0.3 | 33 |

| | | | | | | |
|---|---|---|---|---|---|---|
| Example 10 | 99.488% LLDPE | Calcium oxide (0.012%) | Glycerol monostearate (0.25%) | Crest- 0.5 Trough- 0.7 | 7.5 | 0.3 | 33 |
| Example 11 | 99.49% LLDPE | Calcium oxide (0.01%) | Glycerol monostearate (0.25%) | Crest- 0.4 Trough- 0.7 | 5.5 | 0.3 | 33 |
| Example 12 | 99.488% LLDPE | Calcium oxide (0.012%) | Glycerol monostearate (0.25%) | Crest- 0.5 Trough- 0.7 | 7.5 | 0.3 | 33 |

| Tube examples | Average Condensate accumulation over 16 hrs (grams) | Improvement over existing product, reference sample 1 | Improvement over reference sample 2 | Improvement over reference sample 3 | Heater wire used (yes/no, location e.g. within tube, outside tube, embedded in wall of tube) | Outer sheath used (yes/no) |
|---|---|---|---|---|---|---|
| Reference sample 1 | 127.18 | NA | NA | NA | Internal Coiled Heater | No |
| Reference sample 2 | 93.17 | 26.7% | NA | NA | Internal Coiled Heater | Yes |
| Reference sample 3 | 59.59 | 53.1% | 36.0% | NA | External Filament Heater | Yes |
| Example 1 | 118.11 | 7.1% | −26.8% | −98.2% | Internal Coiled Heater | No |
| Example 2 | 114.93 | 9.6% | −23.4% | −92.9% | Internal Coiled Heater | No |
| Example 3 | 56.85 | 55.3% | 39.0% | 4.6% | External Filament Heater | Yes |
| Example 4 | 115.98 | 8.8% | −24.5% | −94.6 | Internal Coiled Heater | No |
| Example 5 | 105.34 | 17.2% | −13.1% | −76.8% | Internal Coiled Heater | No |
| Example 6 | 81.45 | 36.0% | 12.6% | −36.7% | Internal Coiled Heater | Yes |
| Example 7 | 61.82 | 51.4% | 33.6% | −3.7% | External Filament Heater | Yes |
| Example 8 | 61.43 | 51.7% | 34.1% | −3.1% | External Filament Heater | Yes |
| Example 9 | 90.10 | 29.2% | 3.3% | −51.2% | Internal Coiled Heater | No |
| Example 10 | 83.16 | 34.6% | 10.7% | −39.6% | Internal Coiled Heater | No |
| Example 11 | 70.36 | 44.7% | 24.5% | −18.1% | Internal Coiled Heater | Yes |
| Example 12 | 43.05 | 66.2% | 53.8% | 27.8% | External Filament Heater | Yes |

Component of an Insufflation System

Laparoscopic surgery, also called minimally invasive surgery (MIS), or keyhole surgery, is a modern surgical technique in which operations in the abdomen are performed through small incisions (usually 0.5-1.5 cm) as compared to larger incisions needed in traditional surgical procedures. Laparoscopic surgery includes operations within the abdominal or pelvic cavities.

In abdominal surgery, for example, the abdomen is usually insufflated with carbon dioxide gas to create a working and viewing space. The gas used is generally CO2 which is common to the human body and can be absorbed by tissue and removed by the respiratory system. It is also non-flammable, which is important because electrosurgical devices are commonly used in laparoscopic procedures. The use of these devices tends to create surgical smoke in the working space due to burning of tissue. Smoke evacuation systems which use a discharge arm or limb are commonly used to remove the smoke from the surgical site, so that a surgeon can see what he or she is doing, and so that this potentially harmful material does not remain within the body cavity post-surgery.

A typical smoke evacuation system generally includes a trocar and a cannula at the end to aid insertion into the operative site. The smoke exits the insufflated abdominal area through the discharge limb. The discharge limb may be attached to the end of a laparoscopic instrument so as to provide evacuation close to the site where electrocautery takes place. Usually, the gases and smoke from the body cavity are filtered through a filter to remove particulate matter before they are vented to atmosphere.

It has been common practice in laparoscopic surgery to use dry gases. However, it is also desirable for the CO2 or other insufflation gas to be humidified before they are passed into the abdominal cavity. This can help prevent 'drying out' of the patient's internal organs, and can decrease the amount of time needed for recovery from surgery.

FIG. 4 shows a typical insufflation system 200 such as might be used with the present invention. The insufflation system 200 includes an insufflator 201 that produces a stream of humidified insufflation gases at a pressure above atmospheric for delivery into the patient's abdominal or peritoneal cavity. The insufflation system 200 includes a heater base 204 and humidifier chamber 203, with the chamber 203 in use in contact with the heater base 204 so that the heater base provides heat to the chamber. The insufflation gases are passed through the chamber 203 so that they become humidified to an appropriate level of moisture. The system includes a delivery conduit that connects between the humidification chamber 203 and the peritoneal cavity or surgical site. The conduit has a first end and second end, the first end being connected to the outlet of the humidification chamber 203 and receiving humidified gases from the chamber 203. The second end of the conduit is placed in the surgical site or peritoneal cavity and humidified insufflation gases travel from the chamber 203, through the conduit and into the surgical site to insufflate and expand the surgical site or peritoneal cavity. The conduit can be formed of the tabular component 1 according to this invention and the benefits thereof provided for such a surgical application. The system also includes a controller (not shown) that regulates the amount of humidity supplied to the gases by controlling the power supplied to the heater base 204.

The smoke evacuation system 202 comprises a discharge or exhaust limb 205, a discharge assembly 207 and a filter 206. The discharge limb 205 connects between the filter 206 and the discharge assembly 207, which in use is located in or adjacent to the operative site. The discharge limb 205 is a self-supporting conduit or tube (the conduit is capable of supporting its own weight without collapsing) with two open ends: an operative site end and an outlet end is made of a breathable foamed material as described in this specification.

When saturated gases pass out of the abdominal cavity, they contact the cooler walls of the discharge limb, which is normally around one metre in length or thereabouts and moisture in the gases tends to condense onto the walls of the discharge limb or exhaust conduit. Water vapour can also condense on the filter, which can saturate the filter and cause it to become blocked. This potentially causes an increase in back pressure and hinders the ability of the system to clear smoke.

The present medical tubing as described above with reference to breathing tubes is also suitable for application in the delivery limb of a surgical humidification system. In particular, the medical tubing of the present invention is appropriate for use in the evacuation or exhaust limb of a smoke evacuation system. The performance benefits of the tubing are a result of the improved rainout performance (i.e. less condensation forming) of the tubes of the present invention.

Other Applications

It is anticipated that the present invention will find other medical applications to which it is particularly suited. For example, applications where consistent heating or maintenance of heating of tubing conveying a humid gas in order to reduce the formation of condensation could benefit from the low cost and efficient heating of the present invention.

The foregoing description of the invention includes preferred forms thereof. Modifications may be made thereto without departing from the scope of the invention To those skilled in the art to which the invention relates, many changes in construction and widely differing embodiments and applications of the invention will suggest themselves without departing from the scope of the invention as defined in the appended preliminary claims. The disclosures and the descriptions herein are purely illustrative and are not intended to be in any sense limiting.

What is claimed is:

1. A component forming a part of a breathing tube, or forming the breathing tube, comprising:
   a tubular body having a foamed wall,
   wherein the foamed wall has a void fraction that, in use, enables visual detection of a liquid or a condensate within the tubular body.

2. The component as claimed in claim 1, wherein the foamed wall of the tubular body comprises a corrugate profile, wherein the corrugate profile comprises alternating outer crests and inner troughs.

3. The component as claimed in claim 1, wherein the tubular body has a substantially uniform wall thickness.

4. The component as claimed in claim 1, wherein the wall thickness is about 0.4 mm to about 0.8 mm.

5. The component as claimed in claim 1, wherein the foamed wall has a thermal conductivity of about 0.2 to 0.4 W/m–° K.

6. The component as claimed in claim 1, wherein the foamed wall has a void fraction of about 5.5% to about 7.5%.

7. The component as claimed in claim 1, wherein the tubular body having the foamed wall is formed from extrusion of a single extrudate.

8. The component as claimed in claim 7, wherein the single extrudate comprises one or more polymer(s).

9. The component as claimed in claim 8, wherein the one or more polymer(s) is selected from the group consisting of Linear Low Density Polyethylene (LLDPE), Low Density Polyethylene (LDPE), Polypropylene (PP), Polyolefin Plastomer (POP), Ethylene Vinyl Acetate (EVA), plasticised Polyvinyl chloride (PVC), and blends of these materials.

10. The component as claimed in claim 8, wherein the one or more polymer(s) is at least about 98.4 weight percent (wt. %) of the total single extrudate.

11. The component as claimed in claim 7, wherein the single extrudate further comprises one or more chemical foaming agents.

12. The component as claimed in claim 11, wherein the one or more chemical foaming agents comprising calcium oxide.

13. The component as claimed in claim 11, wherein the chemical foaming agent is at least about 0.005 weight percent (wt. %) of the total single extrudate.

14. The component as claimed in claim 7, wherein the single extrudate further comprises one or more surface modification agents.

15. The component as claimed in claim 1, wherein the tubular body enables surface property contact angles of less than about 45 degrees (°).

16. The component as claimed in claim 1, further comprising a heater.

17. The component as claimed in claim 16, wherein a heater is associated with a wall of the tubular body.

18. The component as claimed in claim 17, wherein the heater is embedded, either partially or wholly, in the wall of the tubular body.

19. The component as claimed in claim 1, wherein the tubular body further comprises an outer sheath.

20. The component as claimed in claim 19, wherein the outer sheath surrounds a heater associated with an exterior wall surface of the tubular body.

* * * * *